(12) United States Patent
Prestel et al.

(10) Patent No.: US 7,931,667 B2
(45) Date of Patent: Apr. 26, 2011

(54) MEDICAL INSTRUMENT

(75) Inventors: Stephan Prestel, Rheinstetten-Mörsch (DE); Frank Knodel, Knittlingen (DE); Carl-Sebastian Wagner, Bretten (DE); Josef Bartolic, Karlsruhe-Grötzingen (DE)

(73) Assignee: Richard Wolf GmbH, Knittlingen (DE)

( * ) Notice: Subject to any disclaimer, the term of this patent is extended or adjusted under 35 U.S.C. 154(b) by 888 days.

(21) Appl. No.: 11/005,143

(22) Filed: Dec. 6, 2004

(65) Prior Publication Data

US 2005/0125026 A1 Jun. 9, 2005

(30) Foreign Application Priority Data

Dec. 6, 2003 (DE) .................... 103 57 103

(51) Int. Cl.
*A61B 17/00* (2006.01)
(52) U.S. Cl. ............ 606/205; 279/66; 279/75; 279/102; 279/906
(58) Field of Classification Search .................. 606/205; 279/74, 75, 82, 905, 29, 30, 904, 906, 22, 279/79, 80; 403/322.2; 285/277, 316; 433/127–129
See application file for complete search history.

(56) References Cited

U.S. PATENT DOCUMENTS

| | | | | |
|---|---|---|---|---|
| 3,465,835 A * | 9/1969 | Krivit | .............................. | 173/170 |
| 4,577,875 A | 3/1986 | Miyakawa | | |
| 4,692,073 A * | 9/1987 | Martindell | ................. | 408/239 A |
| 4,719,976 A * | 1/1988 | Bleicher et al. | ................ | 173/109 |
| 4,828,277 A * | 5/1989 | De Bastiani et al. | ............ | 279/22 |
| 4,998,351 A * | 3/1991 | Hartmeister | ..................... | 30/228 |
| 5,009,661 A * | 4/1991 | Michelson | ...................... | 606/170 |
| 5,441,494 A * | 8/1995 | Ortiz | .................................. | 606/1 |
| 5,505,737 A | 4/1996 | Gosselin et al. | | |
| 5,569,284 A * | 10/1996 | Young et al. | ................... | 606/180 |
| 5,730,372 A * | 3/1998 | Bradley | ........................... | 241/29 |
| 5,957,634 A * | 9/1999 | Carpinetti | ...................... | 408/226 |
| 2001/0017447 A1* | 8/2001 | Baumann et al. | ............ | 279/19.4 |
| 2002/0095177 A1* | 7/2002 | Kupferschmid et al. | ...... | 606/205 |
| 2003/0188877 A1* | 10/2003 | Saur et al. | ........................ | 173/13 |
| 2004/0056435 A1* | 3/2004 | Bedi et al. | ........................ | 279/75 |

FOREIGN PATENT DOCUMENTS

| | | |
|---|---|---|
| DE | 87 09 151.8 U1 | 12/1987 |
| DE | 39 34 610 A1 | 4/1991 |
| DE | 195 14 098 A1 | 10/1996 |
| DE | 198 09 120 C1 | 8/1999 |
| DE | 199 18 638 A1 | 11/2000 |
| DE | 199 30 426 A1 | 1/2001 |
| WO | WO 01/01870 A1 | 1/2001 |

OTHER PUBLICATIONS

Albee, F. "bone Surgery with Machine Tools", Scientific American, Apr. 1936, pp. 178-181.*

* cited by examiner

*Primary Examiner* — Todd E Manahan
*Assistant Examiner* — Jonathan A Hollm
(74) *Attorney, Agent, or Firm* — Panitch Schwarze Belisario & Nadel LLP

(57) ABSTRACT

A medical instrument has an instrument insert (4) and an instrument handle (2) which are detachably connected to one another via a locking connection. A grip (24; 57) and a closure (26; 50) are provided for securing the locking connection. The closure (26; 50) may be moved into an unsecured position by movement of the grip (24; 57) as well as independently of a movement of the grip (24; 57).

14 Claims, 5 Drawing Sheets

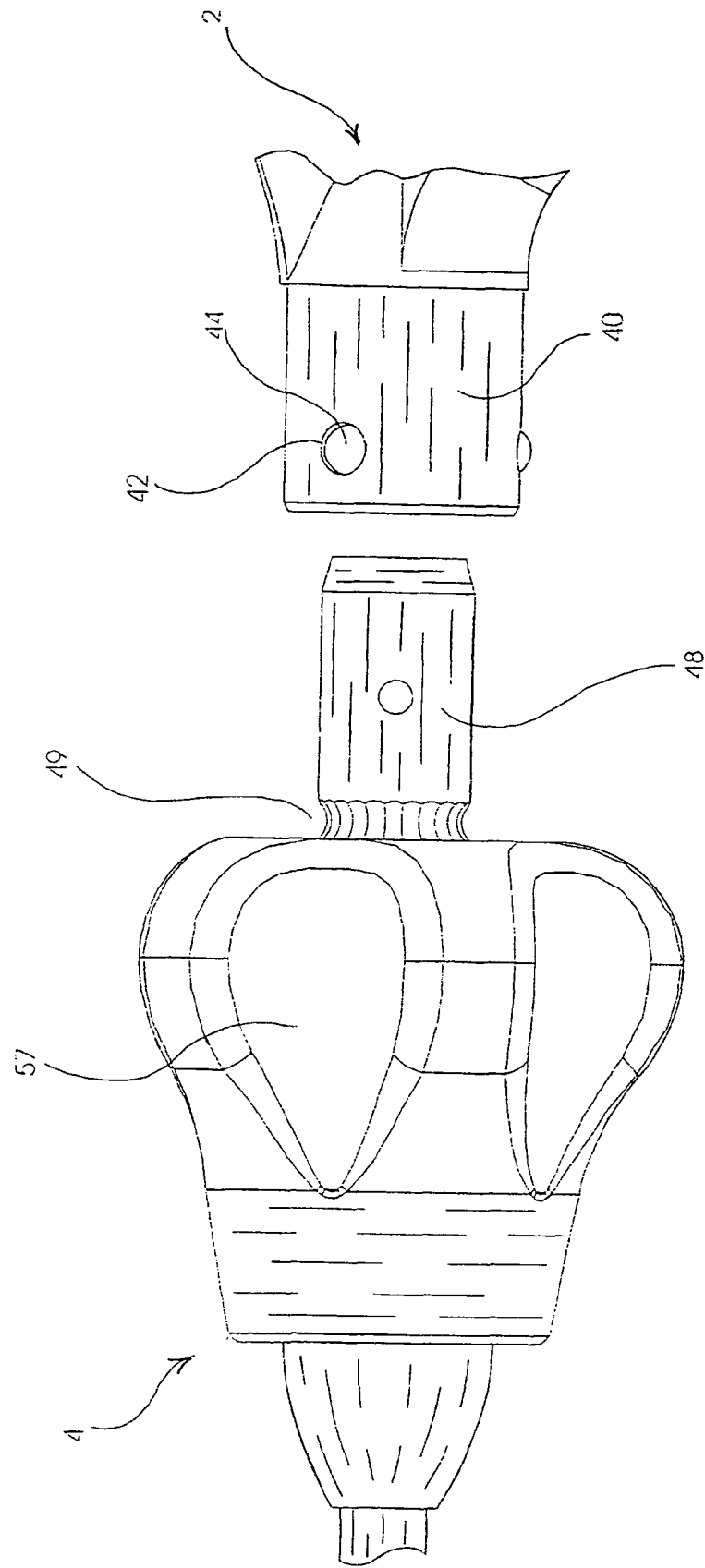

MEDICAL INSTRUMENT

BACKGROUND OF THE INVENTION

The invention relates to a medical instrument, for example a medical forceps, having an instrument insert and an instrument handle.

Medical instruments in which an instrument insert is detachably connectable to an instrument handle are known in the art, for example from German patent DE 198 09 120 C1. In the instrument disclosed in German patent DE 198 09 120 C1, the instrument insert is connected to the instrument handle via a ball locking connection. For locking the ball locking connection, an insert connected to a grip is provided, and this insert is held by a compression spring in a secured position in which the insert blocks the locking balls. For releasing the connection, the grip provided on the instrument handle is moved proximally, so that the insert is moved proximally away from the locking ball and releases the ball. This release movement is required when assembling the instrument insert and the instrument handle, as well as on separating them. In particular, during assembly this locking system is difficult to handle. On the one hand, the grip must be moved proximally in order to bring the insert into its released position, and on the other hand, at the same time, the instrument handle must be moved with the grip distally towards the proximal end of the instrument insert in order to join both parts together. This renders the handling extremely awkward.

BRIEF SUMMARY OF THE INVENTION

It is therefore an object of the invention to provide an improved medical instrument with an instrument insert and with an instrument handle which may be detachably connected to one another via a locking connection, in which the instrument insert and the instrument handle may be more easily assembled and separated.

This object is achieved with the medical instrument according to the invention which comprises an instrument insert and an instrument handle detachably connectable to one another via a locking connection. In a known manner, this permits the instrument to be dismantled for cleaning, and permits the combination of different instrument inserts with one and the same instrument handle, depending on the application purpose. At least one grip and a closure for securing the locking connection are provided for connecting the instrument insert and the instrument handle. At the same time, the grip and closure may be arranged either at the distal end of the instrument handle or at the proximal end of the instrument insert. The closure is arranged such that it may be moved into an unsecured position by movement of the grip, or independently of the movement of the grip, in order to release the locking connection. In this condition, the instrument insert may be separated from the instrument handle or may be connected to the instrument handle.

According to the invention, the closure which secures the locking connection is thus decoupled from the grip, which must be moved for releasing the locking connection. On assembly of the instrument handle and the instrument insert by the engagement of corresponding components of the locking connection, this permits the closure to be moved automatically into the release position without a movement of the grip. Thus, it is no longer necessary, as with previously known arrangements, to also move the grip into a released position on assembly. For example, if the grip and the closure are arranged at the distal end of the handle, it is possible for the instrument handle to be gripped at the grip and to be moved distally together with the grip toward the proximal end of the instrument insert, while the closure is simultaneously moved proximally by the proximal end of the instrument insert without the grip having to be moved jointly in this direction. The grip and the closure may thus execute opposite movements on assembly. A significantly simpler assembly of the instrument insert and the instrument handle is thereby achieved.

For release, the grip may again be gripped and moved into a release position, whereby on movement of the grip, the closure is moved jointly into the released position in order release the locking connection and to separate the instrument insert from the instrument handle. Thus, with the mentioned example, the grip may be moved proximally and the closure may thereby be moved jointly in the proximal direction in order to release the locking connection. A reverse arrangement is also possible if the grip and the closure are arranged at the distal end of the instrument insert. In this case, the closure sleeve is moved in the distal direction into the released position. With all arrangements the grip and closure are decoupled in a manner such that a movement of the grip into the released position simultaneously effects a movement of the closure into the released positioned. However, a movement of the closure does not simultaneously cause a movement of the grip into the released position.

The design according to the invention thus has the advantage that for assembling the instrument handle and the instrument insert, the grip may be used to grip the component connected to it, either the instrument handle or the instrument insert. Subsequently, by moving the grip in the joining direction, the component is moved to the other component of the instrument, in order to connect the components, specifically the instrument handle and the instrument insert. Reversely, for releasing, the grip is gripped in order to move the component connected to it away from the other component. The locking connection is automatically locked or released by the movement which is required in any case for the separation and assembly of the instrument handle and instrument insert. On the one hand, the automatic locking connection between the instrument insert and the instrument handle created in this manner, on axially pushing the instrument insert and the instrument handle together, automatically locks the joined-together components on account of the movement of the closure. On the other hand, these are again automatically unlocked on pulling apart the instrument insert and the instrument handle by moving the grip. No additional securing elements need to be manually released or locked.

The locking connection preferably comprises at least one movable locking element, wherein the closure in a secured position blocks the locking element and in an unsecured position releases the locking element. The locking element may be designed, for example, as a locking projection or a locking body which engages into a corresponding recess, wherein the closure blocks the locking element such that it may not come out of the recess. In the released position, the closure permits a movement of the locking element so that, for example, a locking body or a locking projection disengages from the recess and releases the locking connection, which means that the instrument handle and the instrument insert may be separated from one another.

The locking elements are preferably movable in the radial direction, in order to be able to engage and disengage with corresponding locking elements, for example locking recesses. The closure, which secures the locking elements, is preferably movable in the axial direction in order to secure and release the locking connection. Accordingly, an axially directed locking force is exerted onto the closure. The combination of the axially directed locking force and the radially movable locking elements permits a particularly compact design of the locking connection in comparison to an arrangement with which the locking force is also applied in the radial direction.

The locking element is preferably a locking ball. Such locking balls permit a simple assembly, since they easily slide into corresponding locking recesses. Alternatively the locking element may be designed as a resilient locking tongue. Such locking elements have the advantage that they may be manufactured inexpensively as plastic injection molded parts. Locking projections are formed at the free end of the locking tongues, and these projections may engage into corresponding locking openings or may engage behind corresponding locking projections.

Preferably, the locking elements engage into a corresponding annular locking groove. This permits a rotatable design of the locking connection with which, on assembling the instrument insert and the instrument handle, one does not have to respect a certain angular position, since the locking elements may engage into the annular locking groove at any angular position. Furthermore, such a locking connection allows the locking elements to be rotated in the annular locking groove even in the joined condition so that, for example, the instrument insert may be rotated about its longitudinal axis with respect to the instrument handle.

Preferably, the grip and the closure may be moved in the direction of the longitudinal axis of the instrument insert. This arrangement permits a slim design of the locking connection between the instrument handle and the instrument insert. Furthermore, a simple assembly and separation of the instrument insert and the instrument handle is possible, since the grip and the connection element for releasing and locking, respectively, are moved in the movement direction of the instrument insert and the instrument handle.

The closure is usefully held in the secured position by spring force. One may thereby achieve an automatic securement on assembling the instrument insert and the instrument handle. Furthermore, one may prevent an inadvertent detachment on use of the instrument. The spring force may be effected, for example, by an axially acting helical spring.

The closure is preferably designed as a closure sleeve, and the grip part as a grip sleeve, which are movably guided in the direction of the longitudinal axis of the instrument insert, wherein the closure sleeve is arranged inside of the grip sleeve. This arrangement, on the one hand, permits a rotationally symmetrical design of the locking connection, whereby the rotation ability of the instrument insert with respect to the instrument handle may be achieved. On the other hand, a compact design of the locking connection may be achieved, which permits a slim shaping of the instrument as a whole without disturbing projections or projecting actuation means. The arrangement of the closure sleeve inside of the grip sleeve has the advantage that the closure sleeve is covered to the outside by the grip sleeve, so that the movement of the closure sleeve is not inadvertently blocked on handling the instrument. Furthermore, a danger of injury, for example due to pinching on moving the closure sleeve, is prevented.

It is further preferred for the closure sleeve to comprise at least one contact shoulder, behind which a contact shoulder formed on the grip sleeve engages on only one surface which is rearward in the movement direction towards the unsecured position. This design has the effect that on movement of the grip sleeve toward the unsecured position, the contact shoulder of the grip sleeve comes to bear on the surface of the contact shoulder of the closure sleeve, this surface being rearward in the movement direction, and thus as a catch likewise presses or pushes the closure sleeve in the direction of the unsecured position. Reversely, if the closure sleeve is moved in the direction of the secured position and the grip sleeve was previously likewise located in the unsecured position, the contact shoulder of the closure sleeve presses against the contact shoulder of the grip sleeve and likewise pushes this in the direction of the secured position. This is particularly advantageous when a spring element is provided which pushes the closure sleeve into the secured position, since the spring element thus also holds the grip sleeve in the secured position.

However, since the contact shoulders do not engage behind one another in the opposite direction, the closure sleeve may be moved into the unsecured position without catching the grip sleeve, which means that the grip sleeve may remain in its original position in the secured position. The contact shoulders of the grip sleeve and the closure sleeve are preferably designed such that the contact shoulder of the closure sleeve extends radially outwardly, while the contact shoulder of the grip sleeve is formed on the inner periphery of the grip sleeve. Ideally, both shoulders are formed annularly and in a rotationally symmetrical manner, so that an inexpensive manufacture and a simple assembly of the instrument may be achieved, because one does not have to respect predefined angular positions of the individual components relative to one another.

According to a particular embodiment which is not limited to one of the previously described designs, the locking connection comprises a locking element which, for connecting the instrument insert and the instrument handle, engages into a corresponding locking groove which comprises an axial waved or serrated edge. Such a design of the locking connection allows the locking element to be rotated in the locking groove, wherein a positioning is achieved by the waves or serrations at the edge. Thus, the instrument insert may be rotated in a locking manner with respect to the instrument handle, wherein the slight resistances between the individual locking positions, defined by the waves or serrations, are overcome on rotation.

For this purpose, one may provide a spring element in order to resiliently press the locking element into the waves or serrations of the edge and thus ensure a positioning on rotation. In a medical forceps application, if a force is exerted on the forceps handle, this design permits a force to then act on the shank of the instrument insert via the actuation rod and the forceps jaw, by which the locking element is pressed against the waved or serrated edge, so that it is held in a valley adjacent the edge. It is thereby ensured that on actuation of the instrument, a rotation is no longer possible, but the instrument insert is held in a previously set angular position with respect to the instrument handle. This design may also be applied independently of the above-described features, i.e., particularly independently of the design of the grip and closure sleeve.

Preferably, the grip and the closure are arranged at the proximal end of the instrument insert. Alternatively, however, the invention may also be realized in a manner such that the grip and closure are arranged at the distal end of the instrument handle.

It is particularly preferable to connect the grip to the instrument insert in a torque proof (non rotational) manner. For this purpose, one may provide a suitable linear guide between the grip and the instrument shank of the instrument insert. This permits the instrument insert to be rotated by gripping the grip, for example, in order to connect the instrument insert to the instrument handle at a predetermined angular position with respect to its longitudinal axis. For the case that the connection between the instrument insert and the instrument handle is designed in a rotatable manner, the instrument insert may moreover be gripped at the grip, in order to rotate it with respect to the instrument handle.

According to a further particular embodiment, which may also be realized independently of the previously described embodiments, the instrument insert comprises a shank tube, an actuation rod arranged inside of the shank tube, and at least one element which is arranged at the distal end and may be moved via the actuation rod. This movable element may be, for example, a jaw part of a forceps jaw which is designed at the distal end of the instrument insert. According to this particular embodiment, at least one spring element is arranged as an overload safety device in the transmission path for the movement of the movable element. The spring element has the effect that, in case the actuation force acting on the movable element, for example a forceps jaw, exceeds the spring force, the spring is compressed so that no larger force may be exerted onto the movable element or the forceps jaw. Thereby, on the one hand, damage to the instrument may be avoided, and on the other hand, the instrument may be designed such that tissue parts, for example, may be gripped with a maximal force, which may be preset.

Due to the fact that the spring element is biased with a defined force, until this force is reached this spring element may not be perceived at all on actuation of the instrument over the entire movement space. A fine-touch actuation of the instrument continues to be possible. The spring constant of the spring element is preferably designed such that the bias force, on deformation of the spring element by the path distance which the actuation rod of the instrument may maximally execute, is not increased by more than 20 to 50%. Preferably, the spring element is a compression spring, which extends in the direction of the longitudinal axis of the instrument insert. The arrangement of this overload protection may also be realized independently of the features describe previously. In particular, such an overload protection may also be applied with instruments which have no locking connection between the instrument insert and the instrument handle according to the previously described design.

It is further preferred for the shank tube of the instrument insert at its proximal end to be mounted in a connection element for connection to an instrument handle and to be supported in the proximal direction on the connection element via an axially acting spring element. Such a spring element is preferably a compression spring in the form of a helical spring. With this design, if an actuation rod is moved proximally inside of the shank tube, with the forceps jaw closed, a force likewise acting in the proximal direction is exerted on the shank tube. This force is transmitted via the axially acting spring element onto the connection element to the instrument handle. Then, if the actuation force exerted on the shank tube exceeds the spring force of the spring element, the spring element will deform so that the spring force of the spring element limits the maximum transmittable force. In this manner, the sensitive joints and levers of a forceps jaw may be protected from overload.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 5 is a schematic diagram of an external view of the proximal end of the instrument insert according to FIGS. 2 to 4.

DETAILED DESCRIPTION OF THE INVENTION

Figure 1:
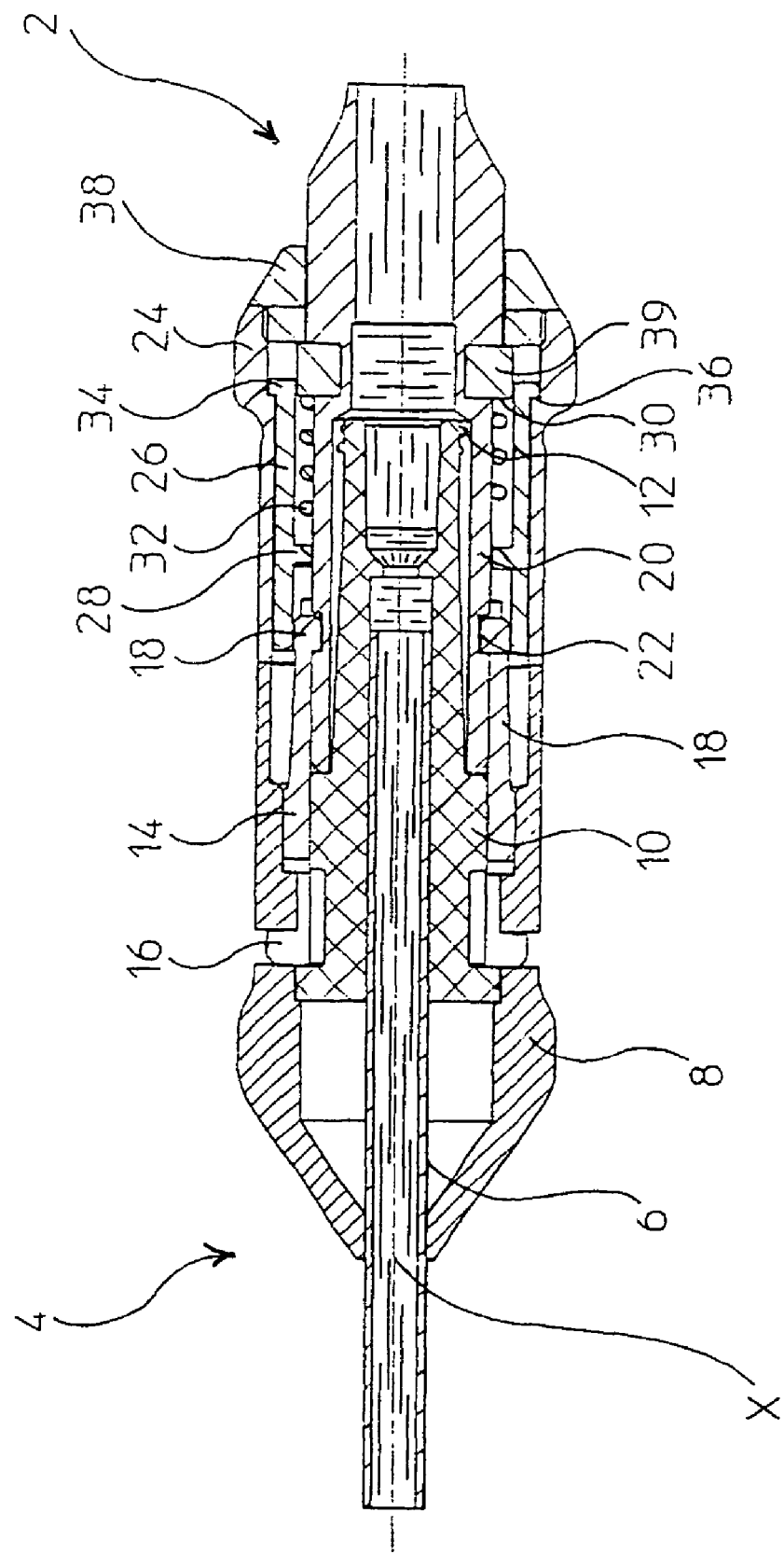
FIG. 1 is a longitudinal sectional view of a locking connection between the instrument insert and the instrument handle, according to a first embodiment of the invention.

FIG. 1 shows a sectional view of the locking connection between an instrument handle 2 and an instrument insert 4, wherein in FIG. 1 only the distal end of the instrument handle 2 and the proximal end of the instrument insert 4 are represented. The instrument insert 4 comprises a shank tube 6 which extends at the proximal end of the instrument insert into a housing part 8 and at its proximal end engages into a connection part 10 and is fixed in this. The proximal end of the connection part 10 is designed as a Luer connection 12 in order to permit a simplified connection of rinsing conduits for cleaning the shank tube 6.

A connection part 14 is inserted into the housing part 8 from the proximal end and is fixed in the housing part 8 via snap hooks 16. The connection part 14 is designed such that besides the snap hooks 16 arranged at the distal end, it comprises snap hooks 18 which extend in the proximal direction which at their proximal free ends comprise radially inwardly directed thickenings in the form of locking projections.

The instrument handle 2 comprises a distally extending housing section 20 in which on the outer periphery an annular locking groove 22 is formed. The thickened sections of locking tongues 18 engage into this locking groove 22 for connection of the instrument handle 2 and the instrument insert 4.

A grip sleeve 24 is guided in an axially movable manner in the direction of the longitudinal axis X at the outer periphery of the housing section 20. A closure sleeve 26 is arranged in the inside of the grip sleeve 24 concentrically to this, and this closure sleeve 26 is likewise guided axially in the direction of the longitudinal axis X on the outer periphery of the housing section 20. The closure sleeve 26 is designed at its distal end such that, in a locking position or secured position, it peripherally engages over the proximal ends of the locking tongues 18, so that the locking tongues 18 may not move radially outwardly. The thickenings of the locking tongues 18 in this position are held firmly engaged with the locking groove 22.

An annular contact shoulder 28 is formed on the inner periphery of the closure sleeve 26. Furthermore, a distally directed contact shoulder 30 is provided on the outer periphery of the housing section 20. The contact shoulder 28 and the contact shoulder 30 are spaced from one another along the direction of the longitudinal axis X, and a compression spring 32 is arranged between the two contact shoulders 28 and 30. The compression spring 32 is designed as a helical spring and is arranged concentrically to the longitudinal axis X. The compression spring 32 presses the closure sleeve 26 via the contact shoulder 28 into its secured position over the locking tongues 18. In this manner, it is ensured that the closure sleeve 26 is moved automatically into the secured position and is held there, so that the locking tongues 18 may not become disengaged from the locking groove 22.

The closure sleeve 26 comprises at the proximal end a radially outwardly directed projection 34. The grip sleeve 24 at its proximal end on the inner periphery is radially widened, so that a proximally directed contact shoulder 36 is formed. A guide element 38, which is movably guided on the outer periphery of the housing section 20 along the direction of the longitudinal axis X, closes the grip sleeve 24 at its proximal end. Furthermore, the guide element 38 at its distal side engages behind the annular projection 39 forming the contact shoulder 30. The projection 39 thus limits the movement of the grip sleeve 24 in the distal direction.

The projection 34 bears with its distally directed side surface on the contact shoulder 36 in the inside of the grip sleeve 24. This has the effect that the grip sleeve 24 is also pushed by the compression spring 32 into the shown secure position via the closure sleeve 26. For releasing the locking connection, the grip sleeve 24 is gripped and moved proximally, whereby the closure sleeve 26 via the contact shoulder 36 and the projection 34 is moved jointly in the proximal direction against the spring force of the compression spring 32. At the same time, the distal end of the closure sleeve 26 becomes disengaged from the locking tongues 18, so that these may move radially outwardly. At the same time, the thickenings of the locking tongues 18 exit radially from the locking groove 22, so that the instrument insert 4 may be separated from the instrument handle 2. If now the grip part 24 is let go, the closure sleeve 26 and the grip part 24 are moved back again into the original locking position via the compression spring 32.

If the instrument handle 2 and the instrument insert 4 are to be assembled together again, then the instrument handle 2 on the grip sleeve 24 and the instrument insert 4 on the housing part 8 may be gripped, and the instrument insert 4 and the instrument handle 2 may be moved towards one another along the direction of the longitudinal axis X. If the instrument insert 4 with the connection part 10 is inserted into the housing section 20 of the instrument insert, the proximal end edges of the locking tongues 18 come to bear on the distal end-face of the closure sleeve 26. With a further movement of the instrument insert 4 towards the instrument handle 2, then the closure sleeve 26 is displaced proximally via the locking tongues 18 against the spring force of the spring 32.

At the same time, the projection 34 is disengaged from the contact shoulder 36 of the grip sleeve 24, so that the grip sleeve remains in its original secured position, while the closure sleeve 26 is displaced proximally to such an extent that the locking tongue 18 may again enter into the locking groove 32. At the same time, the thickenings at the free ends of the locking tongues 18 due to their elasticity move automatically radially inwardly into the locking groove 22, so that the locking tongues 18 may enter into the inside of the closure sleeve 26. At the same time, the distal end-face of the closure sleeve 26 is disengaged from the locking tongues 18, and the closure sleeve 26 is automatically pressed by the compressing spring 32 into the secured position in which the closure sleeve 26 peripherally engages the locking tongues 18 as shown, thus securing these in the locking groove 22. Therefore, on assembly according to the invention, there exists the advantage that the grip sleeve 24 for locking the locking connection does not need to be moved opposite to the movement direction on assembly, but may remain in its original position. The assembly of the instrument is considerably simplified on account of this.

Even though the grip sleeve and the closure sleeve are arranged at the distal end of the instrument handle 2, according to the example according to FIG. 1, the invention may also be realized in a manner such that the grip sleeve and closure sleeve are provided at the proximal end of the instrument insert.

Figure 2:
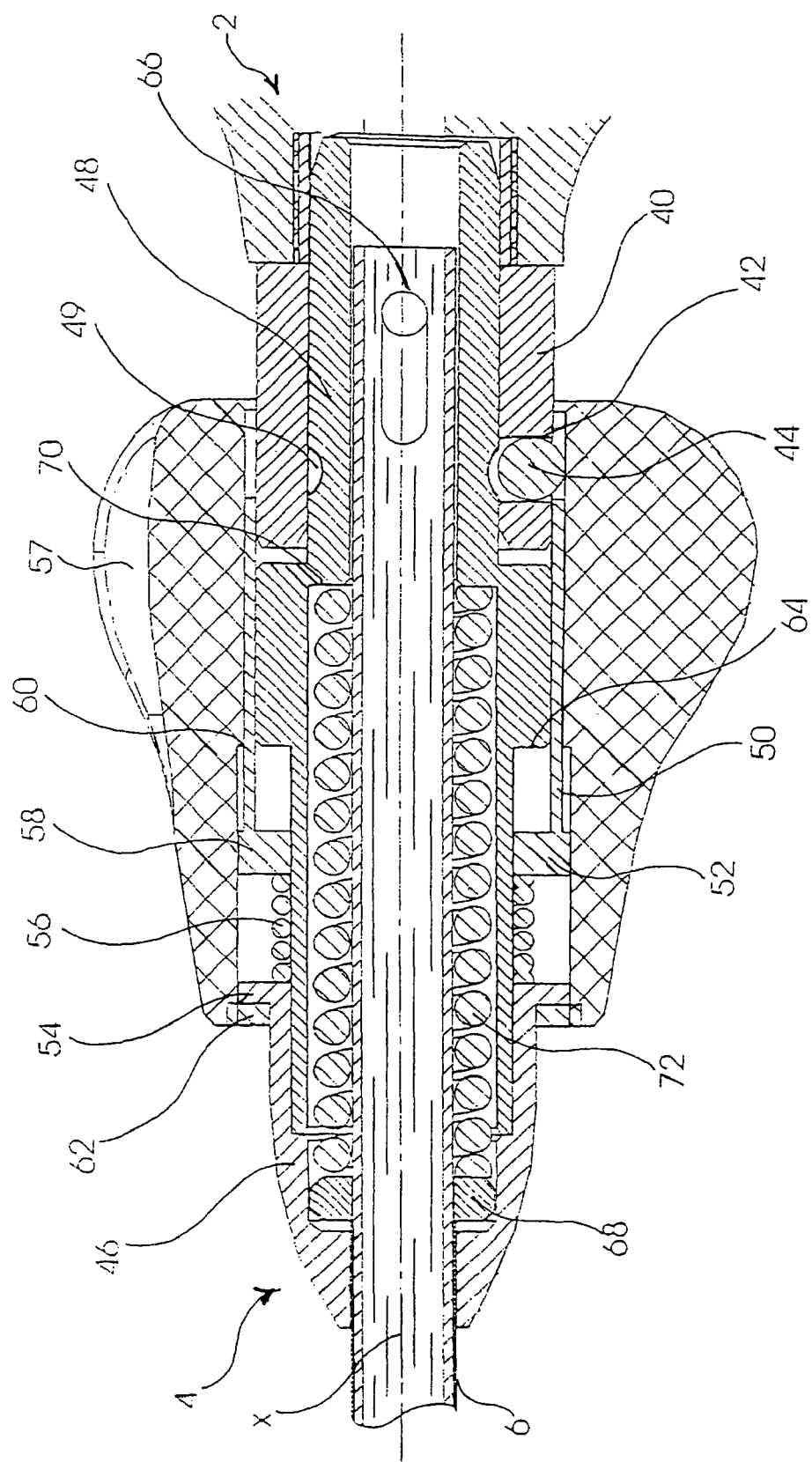
FIG. 2 is a longitudinal sectional view during assembly of a locking connection between the instrument handle and the instrument insert, according to a second embodiment of the invention.

Such a reverse arrangement is provided in the second embodiment, described by FIGS. 2 to 5. FIG. 2 is a sectional view of the locking connection between the instrument handle 2 and the instrument insert 4. A further difference to the embodiment according to FIG. 1 lies in the fact that a ball locking connection is provided in place of locking tongues 18. A sleeve-like housing section 40 extends distally from the instrument handle 2. One or more radially extending bores 42 are formed in the housing section 40, in which locking balls 44 are arranged. The locking balls 44 have a diameter which is larger than the radial extension of the bores 42 and the wall thickness of the housing section 40 respectively.

The instrument insert 4 comprises a shank tube 6 which at its proximal end enters into a housing part 46. The housing part 46 at its proximal end merges into a firmly connected connection part 48. An annular locking groove 49 is formed in a proximal section of the connection part 48 on its outer periphery, into which the locking balls 44 may engage in a locking manner. If the locking balls 44 engage into the locking groove 49, the instrument handle 2 and the instrument insert 4 are firmly connected to one another. For securing this locking connection there is provided a closure sleeve 50 which is guided on the outer periphery of the connection part 48 in the longitudinal direction X. In a locking position, the proximal end of the closure sleeve 50 covers the bores 42, so that the locking balls 44 are held in engagement with the locking groove 49. If the closure sleeve 50 is moved into the released or unsecured position shown in FIG. 2, the proximal end of the closure sleeve 50 frees the bores 42, so that the locking balls 44 may move radially outwardly when the instrument insert 4 is to be removed from the instrument handle 2.

At the distal end, the closure sleeve 50 comprises a radially inwardly directed projection 52, which likewise is guided on the outer periphery of the connection part 48 in a sliding manner. The housing part 46 at its proximal end comprises a radially outwardly directed protrusion 54. A compression spring 56 in the form of a helical spring is arranged parallel to the longitudinal axis X between the protrusion 54 and the projection 52. The compression spring 56 presses the closure sleeve 52 proximally into the locked position in which the bores 42 are covered at their outer periphery by the closure sleeve 50.

The closure sleeve 50 is surrounded by a grip sleeve 57, which is movably guided in the longitudinal direction X on the outer peripheries of the housing part 46 and the closure sleeve 50. The closure sleeve 50 at the position of the projection 52 further comprises an outwardly directed protrusion 58 which butts against the inner periphery of the grip sleeve 57. On the inner periphery of the grip sleeve 57 there is formed a distally directed contact shoulder 60, which serves as an abutment for the protrusion 58 of the closure 50. If the closure sleeve 50 is proximally pressed via the compression spring 56, the protrusion 58 comes to bear on the contact shoulder 60, whereby the grip sleeve 57 is likewise pressed by the compression spring 56 into a locked position and is held there. At the same time, the grip sleeve 57 comprises at its distal end a radially inwardly directed protrusion 62 as an abutment which comes to bear on the distal side of the protrusion 54 of the housing part 46 and thus limits the movement of the grip sleeve 57 in the proximal direction.

The arrangement according to FIG. 2 also permits the decoupled movement of the closure sleeve 50 and the grip sleeve 57. If the instrument handle 2 and the instrument insert 4 are pushed together, the locking balls 44 first slide on the outer periphery of the connection part 48, wherein they project radially outwardly out of the bores 42. At the same time, the locking balls 44 come into contact with the proximal end face of the closure sleeve 50 and push this against the spring force of the compression spring 56 in the distal direction into an unlocked position. At the same time, the protrusion 58 is disengaged from contact shoulder 60 of the grip sleeve 57. The grip sleeve 57 may thus remain in its original position, and the instrument insert 4 which is gripped at the grip sleeve 57 may be moved without problem further proximally towards the instrument handle 2.

When the locking balls 44, on movement in the direction of the longitudinal axis X, reach the position of the locking groove 49, the locking balls 44 may enter into the locking groove 49, whereby the closure sleeve 50 is moved proximally by the compression spring 56 and at the same time presses the locking balls 44 into the locking groove 50. The movement of the closure sleeve 50 in the proximal direction is limited by a step 64 on the outer periphery of the connection part 48. If the projection 52 bears on the step 64, the closure sleeve 50 has reached the locked position shown in FIG. 3 in which it covers the bores 42 and secures the locking balls 44 in the locking groove 49. Simultaneously, the protrusion 58 bears on the contact shoulder 60, and this likewise holds the grip sleeve 57 in its proximal position.

The embodiment shown in FIG. 2 further comprises an overload securement for the actuation of a movable element at the distal end of the instrument insert 4. An actuation rod 66 is arranged in the inside of the shank tube 6, which may be moved proximally, for example in order to close a forceps jaw at the distal end of the instrument insert 4. A portion of the shank tube 6 near the distal end of the housing part 46 comprises a radially outwardly protruding ring element 68. A compression spring 72 is arranged between the proximal side of the ring element 68 and a distally directed contact shoulder 70 inside the connection part 48, and this spring serves as an overload protection.

If the actuation rod 66 is moved proximally in order to close a forceps jaw at the distal end of the shank tube 6, then via the closed forceps jaw and, as the case may be, any element gripped by this, for example a tissue part, a force is exerted on the shank tube 6 in the proximal direction. This force is transmitted in the proximal end portion of the shank tube 6 via the ring element 68 onto the compression spring 72 and from this onto the connection parts 48 and via this further to the instrument handle 2. If the force transmitted then exceeds the spring force of the compression spring 72, the spring 72 is compressed and thus limits the transmittable force. In this manner sensitive elements, joints or levers of the forceps jaw may be protected from overload. The spring constant of the compression spring 72 is preferably selected such that with the maximum possible compression in the instrument, the spring force is not increased by more than 20 to 50%. The overload securement designed in such a manner may also be realized with other instruments which do not have the described locking connections.

Figure 3:
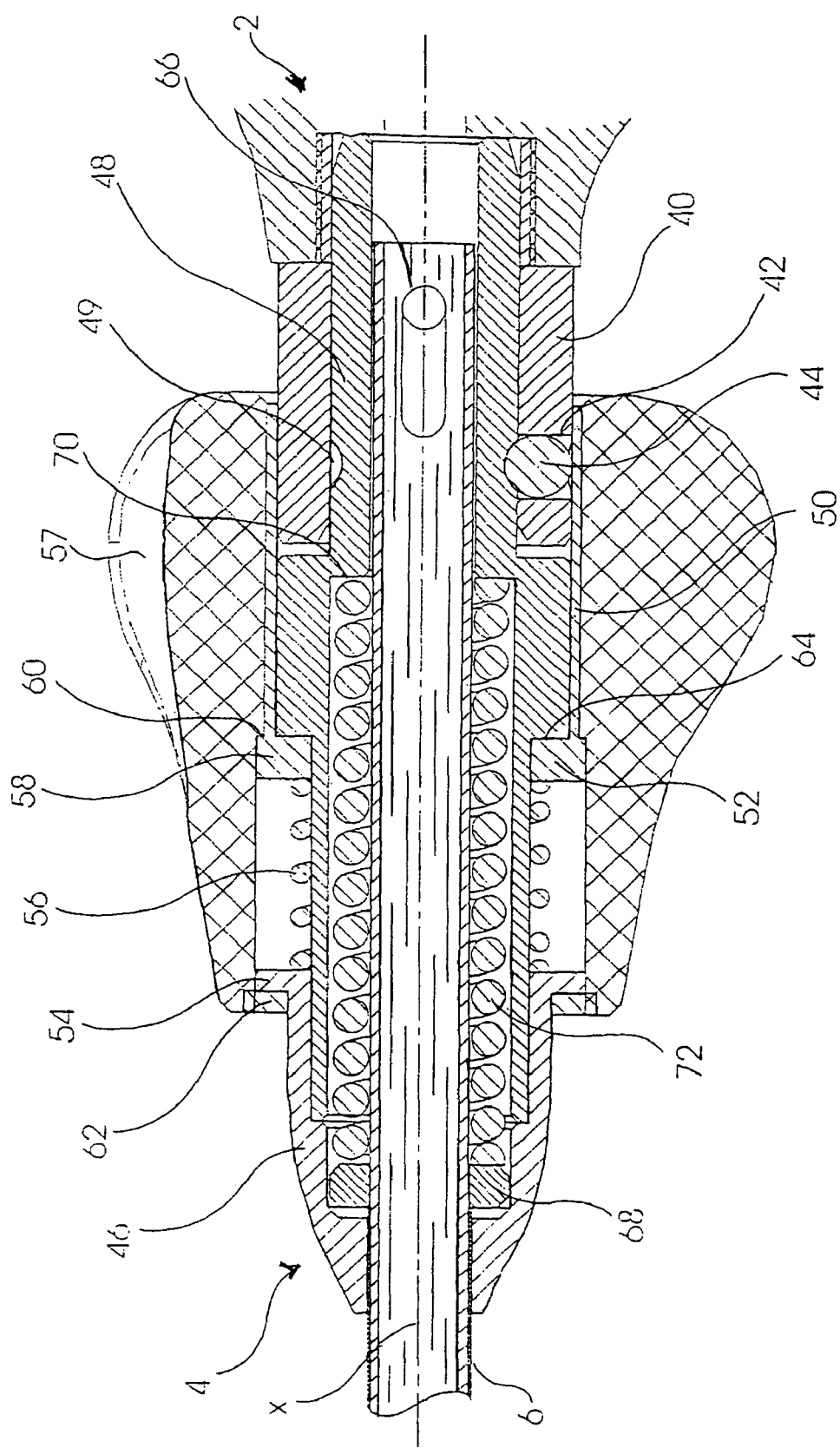
FIG. 3 is another view of the locking connection according to FIG. 2 but in the locked condition.

FIG. 3 shows the completely locked condition of the locking connection according to FIG. 2. The closure sleeve 50 covers the bores 42 so that the locking balls 44 are held securely in the locking groove 49. As described previously, the compression spring 56 holds the closure sleeve 50 and the grip sleeve 57 in this secured position. Otherwise, the preceding description is referred to.

Figure 4:
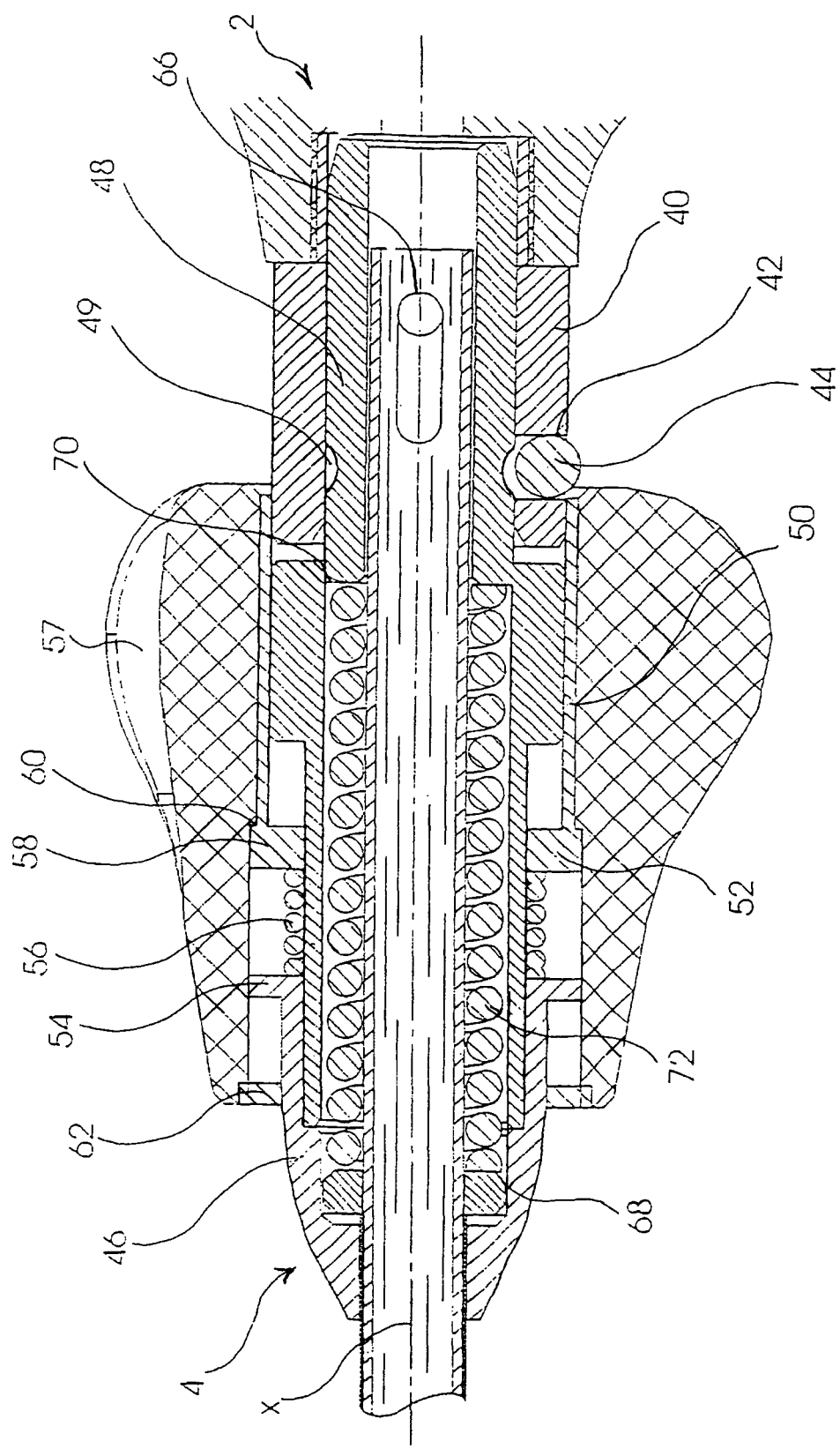
FIG. 4 is a further view of the locking connection according to FIGS. 2 and 3 on separating the instrument insert and the instrument handle.

FIG. 4 shows how the locking connection according to FIGS. 2 and 3 is released. Proceeding from the secured condition shown in FIG. 3, the instrument handle 2 and the grip sleeve 57 of the instrument insert 4 are gripped and pulled apart. At the same time, the grip sleeve 57 is moved distally and via the contact shoulder 60 and the protrusion 58 catches the closure sleeve 50, so that the closure sleeve 50 is moved away from the bores 42 and releases the locking balls 44 so that these may move radially outwardly. Thus the locking balls 44 are disengaged from the locking groove 49 and the instrument insert 4 may be pulled from the instrument handle 2.

The grip sleeve 57 functions simultaneously as a rotation wheel and for this purpose is guided on the housing part 46 of the instrument insert in a rotationally fixed manner. This allows the whole instrument insert to be rotated by rotating the grip sleeve 57 about the longitudinal axis X with respect to the instrument handle 2. At the same time, the locking balls 44 may rotate in the annular locking groove 49.

FIG. 5 shows a non-sectional view of the proximal end of the instrument insert 4 and the distal end of the instrument handle 2, according to the embodiments represented in the FIGS. 2 to 4. As recognized in FIG. 5, the locking groove 49 is designed with a waved configuration, which means, in particular, that it has waved or serrated edges in the axial direction. The effect of this is that with a slight load on rotating the rotation wheel or the grip sleeve 57 relative to the instrument handle 2, one may feel circumferential locking positions, so that the instrument 4 may be rotated with respect to the instrument handle 2 in a locking manner. If the load increases, for example when a jaw part at the distal end of the instrument insert 4 is closed via the actuation rod 66, the locking balls 44 are firmly held in the wave troughs or valleys adjacent the serrated edge of the locking groove 49, so that they may no longer be moved peripherally in the groove 49. Thus the rotation of the instrument insert 4 is blocked on actuation of the actuation rod 66, that is to say, for example, on gripping. This design of the annular groove 49 may also be applied independently of the previously described design with the closure sleeve 50 and the grip sleeve 57.

With the embodiments according to FIGS. 2 to 5, the grip sleeve 57 and the closure sleeve 50 could be arranged instead with a suitable design on the instrument handle 2.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A medical instrument comprising an instrument insert (4) and an instrument handle (2) which are detachably connectable to one another via a locking connection, one of the insert (4) and the handle (2) being provided with a grip (24; 57) and a closure sleeve (26; 50), the closure sleeve being movable between a secured position and an unsecured position, the grip and the closure sleeve being decoupled such that the closure sleeve (26; 50) is movable into the unsecured position by movement of the grip (24; 57) for detaching the handle and the insert and is movable into the secured position independently of a movement of the grip (24; 57) for connecting the handle and the insert, wherein the locking connection comprises at least one movable locking element (18; 44), and the closure sleeve (26; 50) in the secured position blocks the locking element (18; 44) and in the unsecured position releases the locking element (18; 44).

2. The medical instrument according to claim 1, wherein the locking element is a locking ball (44).

3. The medical instrument according to claim 1, wherein the locking element is a resilient locking tongue (18).

4. The medical instrument according to claim 1, wherein the locking element (18; 44) engages into a corresponding annular locking groove (22; 49).

5. The medical instrument according to claim 1, wherein the grip (24; 57) and the closure sleeve (26; 50) are movable in a direction of a longitudinal axis (X) of the insert (4).

6. The medical instrument according to claim 1, wherein the closure sleeve (26; 50) is held in the secured position by a spring force.

7. The medical instrument according to claim 1, wherein the grip (24; 57) comprises a grip sleeve, wherein the closure sleeve and the grip sleeve are movably guided in a direction of a longitudinal axis (X) of the insert (4), and wherein the closure sleeve is arranged inside of the grip sleeve.

8. The medical instrument according to claim 7, wherein the closure sleeve comprises at least one contact shoulder (34; 58) behind which a contact shoulder (36; 60) formed on the grip sleeve engages only on a surface which is rearward in the movement direction to the unsecured position.

9. The medical instrument according to claim 1, wherein the locking element (44) for connection of the insert (4) and the handle (2) engages into a corresponding locking groove (49) which axially comprises a waved or serrated edge.

10. The medical instrument according to claim 1, wherein the grip (57) and the closure sleeve (50) are arranged at a proximal end of the insert (4).

11. The medical instrument according to claim 1, wherein the grip (57) is connected to the instrument insert (4) in a rotationally fixed manner.

12. A medical instrument comprising an instrument insert (4) and an instrument handle (2), the insert (4) comprising a shank tube (6), an actuation rod (66) arranged inside of the shank tube, and at least one element arranged at a distal end of the shank tube (6) and movable via the actuation rod (66), the insert (4) and the handle (2) being detachably connectable to one another via a locking connection, one of the insert (4) and the handle (2), provided with a grip (24; 57) and a closure sleeve (26; 50), the closure sleeve being movable between a secured position and an unsecured position, the grip and the closure sleeve being decoupled such that the closure sleeve (26; 50) is movable into the unsecured position by movement of the grip (24; 57) for detaching the handle and the insert and is movable into the secured position independently of a movement of the grip (24; 57) for connecting the handle and the insert, wherein the locking connection comprises at least one movable locking element (18; 44), and the closure sleeve (26; 50) in the secured position blocks the locking element (18; 44) and in the unsecured position releases the locking element (18; 44).

13. The medical instrument according to claim 12, wherein at least one spring element (72) is arranged as an overload securement in a transmission path for movement of the movable element.

14. The medical instrument according to claim 13, wherein the shank tube (6) is mounted at its proximal end in a connection element (48) for connection to the handle (2), and wherein the shank tube (6) is supported in a proximal direction on the connection element (48) via the spring element (72) acting axially.

* * * * *